(12) United States Patent
Yamashiro et al.

(10) Patent No.: US 8,877,165 B2
(45) Date of Patent: Nov. 4, 2014

(54) SOLID PREPARATION FOR ORAL APPLICATION

(75) Inventors: Takahisa Yamashiro, Sumida-ku (JP); Kazuhiko Kato, Sumida-ku (JP); Shigeto Kayane, Sumida-ku (JP); Junji Nakamura, Haga-gun (JP)

(73) Assignee: Kao Corporation, Tokyo (JP)

( * ) Notice: Subject to any disclaimer, the term of this patent is extended or adjusted under 35 U.S.C. 154(b) by 1322 days.

(21) Appl. No.: 12/293,554

(22) PCT Filed: Apr. 12, 2007

(86) PCT No.: PCT/JP2007/000405
§ 371 (c)(1),
(2), (4) Date: Sep. 19, 2008

(87) PCT Pub. No.: WO2007/122813
PCT Pub. Date: Nov. 1, 2007

(65) Prior Publication Data
US 2010/0226866 A1 Sep. 9, 2010

(30) Foreign Application Priority Data

Apr. 14, 2006 (JP) ................................. 2006-111513

(51) Int. Cl.
| A61K 8/00 | (2006.01) |
|---|---|
| A61Q 11/00 | (2006.01) |
| A61K 45/06 | (2006.01) |
| A61K 8/24 | (2006.01) |
| A61K 31/726 | (2006.01) |
| A61K 8/34 | (2006.01) |
| A61K 31/715 | (2006.01) |
| A61K 33/42 | (2006.01) |
| A61K 8/73 | (2006.01) |
| A61K 8/55 | (2006.01) |
| A61K 9/00 | (2006.01) |
| A61K 9/20 | (2006.01) |

(52) U.S. Cl.
CPC ............... *A61Q 11/00* (2013.01); *A61K 45/06* (2013.01); *A61K 8/24* (2013.01); *A61K 9/2018* (2013.01); *A61K 31/726* (2013.01); *A61K 8/345* (2013.01); *A61K 31/715* (2013.01); *A61K 33/42* (2013.01); *A61K 8/73* (2013.01); *A61K 8/55* (2013.01); *A61K 9/0056* (2013.01)
USPC .......................................................... 424/49

(58) Field of Classification Search
CPC ........... A61K 8/24; A61K 8/345; A61K 8/73; A61K 9/2018; A61K 31/726
See application file for complete search history.

(56) References Cited

U.S. PATENT DOCUMENTS

| 3,886,266 | A | | 5/1975 | Goldman et al. |
|---|---|---|---|---|
| 4,081,526 | A | * | 3/1978 | Asakawa et al. ................ 424/57 |
| 4,855,128 | A | | 8/1989 | Lynch et al. |
| 5,578,299 | A | | 11/1996 | Starch |
| 5,914,118 | A | * | 6/1999 | Yamamura et al. ........... 424/402 |
| 2003/0072719 | A1 | | 4/2003 | Nelson et al. |
| 2003/0152524 | A1 | * | 8/2003 | Eshita ............................. 424/49 |
| 2004/0022745 | A1 | | 2/2004 | Nelson et al. |
| 2004/0033204 | A1 | | 2/2004 | Ahn et al. |
| 2005/0084551 | A1 | | 4/2005 | Jensen et al. |
| 2006/0153780 | A1 | | 7/2006 | Nelson et al. |
| 2006/0159631 | A1 | | 7/2006 | Buch et al. |

FOREIGN PATENT DOCUMENTS

| CN | 1489452 A | 4/2004 |
|---|---|---|
| JP | 49 85249 | 8/1974 |
| JP | 52-57339 | 5/1977 |
| JP | 60 169413 | 9/1985 |
| JP | 1 213222 | 8/1989 |
| JP | 1-268628 | 10/1989 |
| JP | 4-217613 | 8/1992 |
| JP | 5-139979 | 6/1993 |
| JP | 7 17841 | 1/1995 |
| JP | 7 17842 | 1/1995 |
| JP | 8-175968 | 7/1996 |
| JP | 9-235220 | 9/1997 |
| JP | 2000 281551 | 10/2000 |
| JP | 2002 47160 | 2/2002 |
| JP | 2003 2815 | 1/2003 |
| JP | 2004 51535 | 2/2004 |
| JP | 2005-8579 | 1/2005 |
| JP | 2006 188497 | 7/2006 |
| JP | 2007 45796 | 2/2007 |
| WO | 2004 082500 | 9/2004 |
| WO | 2005 030141 | 4/2005 |

OTHER PUBLICATIONS

Alberto E. Veksler, et al., "Reduction of Salivary Bacteria by Pre-Procedural Rinses With Chlorhexidine 0.12 %", J. Periodontal, vol. 62, No. 11, 1991, pp. 649-651.
F.K.L. Spijkervet, DDS, PhD, et al., "Chlorhexidine inactivation by saliva", Oral Surg. Oral Med. Oral Pathol., vol. 69, No. 4, Apr. 1990.
Japanese Office Action issued Jan. 25, 2012, in Japan Patent Application No. 2006-111513 (with English translation).

* cited by examiner

*Primary Examiner* — Snigdha Maewall
(74) *Attorney, Agent, or Firm* — Oblon, Spivak, McClelland, Maier & Neustadt, L.L.P.

(57) ABSTRACT

Provided is a solid preparation for oral application containing (a) gum tragacanth and (b) a polyphosphoric acid or salt thereof and constituted so that the polyphosphoric acid or salt thereof starts to dissolve firstly and the gum tragacanth starts to dissolve subsequently. The solid preparation for oral application according to the present invention has a high plaque formation inhibiting effect.

16 Claims, 2 Drawing Sheets

US 8,877,165 B2

SOLID PREPARATION FOR ORAL APPLICATION

FIELD OF THE INVENTION

The present invention relates to a solid preparation for oral application having an excellent plaque formation inhibiting effect.

BACKGROUND OF THE INVENTION

Plaque and calculi formed by calcification of plaque are causes of various oral diseases such as dental caries and periodontal diseases; therefore, a variety of plaque formation inhibitors and calculus formation inhibitors are proposed for the purpose of preventing such diseases. Plaque is a viscous mass attached to tooth surfaces and it is composed of oral flora and products thereof. The formation of plaque starts with the formation of a pellicle (acquired pellicle) made of saliva components on tooth surfaces. The pellicle is a build-up with amorphous patterns formed on tooth surfaces and saliva components such as sugar protein are adsorbed selectively onto the tooth surfaces. Plaque is formed as a result of adsorption and proliferation of bacteria in the oral cavity on the surface of the pellicle. Moreover, when rod-shaped bacteria such as those belonging to the genera *Fusobacterium* are adsorbed to other bacteria which have already been adsorbed to tooth surfaces, plaque formation is accelerated by the so-called coaggregation, that is, an adsorption reaction among bacteria in the oral cavity.

Bactericides and antimicrobial agents have conventionally been used widely as plaque formation inhibitors, and their effects, including an effect of reducing the number of bacteria in the oral cavity, are reported (Non-patent Document 1). It is however difficult to keep the effective concentration of them in the oral cavity because of a washing action of the saliva, so their effects are insufficient (Non-patent Document 2). Where plaque is already present, these agents weaken the metabolic activity of plaque bacteria, thus facilitating the deposition of minerals, i.e., calcification. As agents for inhibiting adsorption of bacteria to a pellicle, polysaccharides such as funoran and gellan gum are proposed (Patent Document 1). These agents, however, do not inhibit the formation of the pellicle per se; therefore, sometimes their effects are not satisfactory. As a calculus formation inhibitor, use of phosphorylated starch (Patent Document 2) and combined use of alginic acid and a divalent metal (Patent Document 3) are proposed. These inhibitors are used for symptomatic therapy and each of them can prevent only the crystallization of calcium phosphate and the like in plaque into calculi.

Polysaccharides such as xanthan gum, gum tragacanth, and sodium alginate are known to be useful as plaque formation inhibitors capable of inhibiting coaggregation of bacteria in the oral cavity (Patent Document 4).

[Patent Document 1] JP-A-05-139979
[Patent Document 2] JP-A-04-217613
[Patent Document 3] JP-A-08-175968
[Patent Document 4] JP-A-01-213222
[Non-patent Document 1] J. Periodental., 62(11), 649-651 (1991)
[Non-patent Document 2] Oral Surg. Oral Med. Oral Pathol., April; 69(4), 444-449(1990)

SUMMARY OF THE INVENTION

In one aspect of the present invention, there is thus provided a solid preparation for oral application which contains gum tragacanth as Component (a) and a polyphosphoric acid or salt thereof as Component (b) and is constituted so that the polyphosphoric acid or a salt thereof starts to dissolve firstly and the gum tragacanth starts to dissolve subsequently.

In another aspect of the present invention, there is also provided a solid preparation for oral application which contains the above-described Component (a) and Component (b), and one or more sugar alcohols selected from erythritol, xylitol, and sorbitol as Component (c) and is constituted so that the polyphosphoric acid or a salt thereof starts to dissolve firstly and the gum tragacanth starts to dissolve subsequently.

In a further aspect of the present invention, there is also provided a plaque formation inhibiting method containing applying gum tragacanth as Component (a) and a polyphosphoric acid or salt thereof as Component (b) to an oral cavity, wherein the polyphosphoric acid or salt thereof is applied prior to the gum tragacanth.

DETAILED DESCRIPTION OF THE INVENTION

Figure 1:
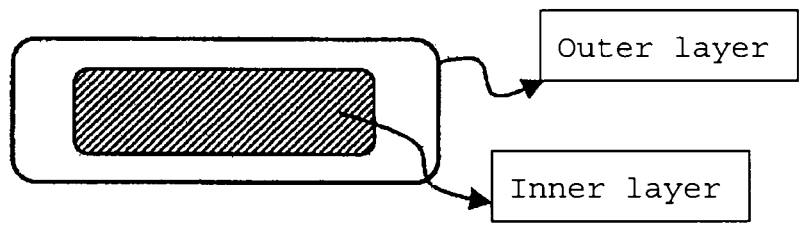
FIG. 1 is a cross-sectional schematic view of a solid preparation having an inner layer and an outer layer.

The present invention provides a solid preparation for oral application having an excellent plaque formation inhibiting effect.

The above-described Patent Document 4 describes that gum tragacanth has a coaggregation inhibiting effect of bacteria in the oral cavity and a plaque formation inhibitor at a concentration of 0.35% can inhibit the coaggregation of bacteria in the oral cavity by 50% compared with the coaggregation which occurs when a tragacanth-free inhibitor is applied. The coaggregation inhibiting effect described in Patent Document 4 is however confirmed by a test in a phosphate buffer. The present inventors therefore paid attention to the coaggregation inhibiting effect of gum tragacanth on bacteria in the oral cavity in the presence of saliva, in terms of the conditions to be used in practice. As a result, it has been elucidated that these polysaccharides cannot suppress coaggregation of bacteria in the oral cavity at such a high rate as to produce a plaque formation inhibiting effect sufficiently in the presence of saliva.

The present inventors therefore investigated an inhibiting effect of gum tragacanth on the adsorption of bacteria to tooth surfaces in the presence of saliva. As a result, they have found unexpectedly that addition of gum tragacanth at a concentration of from 0.0005 to 0.1 mass %, which is too low to efficiently inhibit coaggregation of bacteria in the presence of saliva, suppresses adsorption of bacteria to tooth surfaces strongly and such a composition is therefore useful as a plaque formation inhibitor. The present inventors moved forward with a further investigation and arrived at the finding that although single use of a polyphosphoric acid or salt thereof is not effective for suppressing plaque formation, use of it with gum tragacanth brings about a drastically improved plaque formation inhibiting effect. The present inventors also found that a preparation having a good taste and an excellent plaque formation inhibiting effect could be obtained using these two components with a specific sugar alcohol in combination.

Plaque formation can be inhibited effectively by using a solid preparation for oral application according to the present invention which contains gum tragacanth and a polyphosphoric acid or salt thereof. At the same time, the solid preparation is constituted so that the polyphosphoric acid or salt thereof starts to dissolve firstly and the gum tragacanth starts to dissolve subsequently. Moreover, when the solid preparation for oral application is containing a sugar alcohol, in addition to gum tragacanth and a polyphosphoric acid or salt thereof, inhibition of plaque formation and improvement in taste can be satisfied simultaneously.

The solid preparation for oral application according to the present invention contains gum tragacanth and a polyphosphoric acid or salt thereof. The polyphosphoric acid or salt thereof does not have a plaque formation inhibiting effect when any of them is used singly. However, combined use of the polyphosphoric acid or salt thereof with gum tragacanth enhances a bacteria-adsorption inhibiting effect of gum tragacanth to tooth surfaces and a plaque formation inhibiting effect. Examples of the polyphosphoric acid usable in the present invention include pyrophosphoric acid, acidic pyrophosphoric acid, and tripolyphosphoric acid. As the salt of the polyphosphoric acid, alkali metal salts such as sodium salts and potassium salts can be used. Specific examples include condensed phosphates such as sodium pyrophosphate, acidic sodium pyrophosphate, and sodium tripolyphosphate.

A content of gum tragacanth in the solid preparation for oral application is preferably from 0.001 to 10 mass %, more preferably from 0.1 to 8 mass %, even more preferably from 0.1 to 5 mass % from the viewpoint of a plaque formation inhibiting effect. A content of the polyphosphoric acid or salt thereof in the solid preparation for oral application is preferably from 0.001 to 10 mass %, more preferably form 0.01 to 5 mass %, even more preferably from 0.05 to 2 mass % from the viewpoint of a plaque formation inhibiting effect.

The solid preparation of the present invention is constituted, in order to inhibit plaque formation effectively, so that the polyphosphoric acid or salt thereof starts to dissolve firstly and the gum tragacanth starts to dissolve subsequently. The phrase "the polyphosphoric acid or salt thereof starts to dissolve firstly" as used herein means that when the solid preparation of the present invention is applied, it is only necessary that a layer containing the polyphosphoric acid or salt thereof is brought into contact with the oral cavity firstly; in the case where a layer containing the gum tragacanth and another layer containing the polyphosphoric acid or salt thereof are brought into contact with the oral cavity simultaneously, it is only necessary that the preparation is constituted so that the layer containing the polyphosphoric acid or salt thereof has a greater surface area in the whole surface area of the solid preparation or the polyphosphoric acid or salt thereof dissolves earlier; or in the case where both the gum tragacanth and the polyphosphoric acid or salt thereof are contained in a layer to be brought into contact with the oral cavity first, it is only necessary that the preparation is constituted so that the concentration of the polyphosphoric acid or salt thereof is higher than that of the gum tragacanth. Examples of such a preparation include a solid preparation obtained by covering the gum tragacanth with the polyphosphoric acid or salt thereof; a solid preparation having the gum tragacanth dispersed in the polyphosphoric acid or salt thereof; and a solid preparation having a gum tragacanth layer sandwiched between layers containing the polyphosphoric acid or salt thereof.

The solid preparation for oral application according to the present invention has an excellent plaque formation inhibiting effect and an improved taste by containing therein a specific sugar alcohol. The sugar alcohol of the present invention is selected from erythritol, xylitol, and sorbitol. Use of erythritol is preferred from the viewpoint of improving the plaque formation inhibiting effect. Erythritol has three isomers, that is, L-erythritol, D-erythritol, and meso-erythritol, and any of them is usable.

A content of the sugar alcohol in the solid preparation for oral application is preferably from 18 to 85 mass %, more preferably from 20 to 70 mass %, even more preferably from 25 to 60 mass %, far more preferably from 28 to 50 mass % from the viewpoint of improving the taste and giving an excellent plaque formation inhibiting effect.

The sugar alcohol may be incorporated with either of the gum tragacanth or the polyphosphoric acid or salt thereof; however, it is preferred from the viewpoint of improving the taste that it starts to dissolve simultaneously with the polyphosphoric acid or salt thereof.

The solid preparation can be obtained by mixing the above-described components with an excipient and then treating the mixture in a manner known per se in the art. Excipients used for ordinary solid preparations for oral cavity can be employed. Examples include lactose, starch, dextrins, celluloses, polyethylene glycol, magnesium stearate, and maltitol and the like.

A content of the excipient in the preparation is preferably 80 mass % or less, more preferably from 5 to 75 mass %.

Although the form of the solid preparation of the present invention is not particularly limited, examples include tablets, pills, and granules and the like. Of these, tablets are preferred.

The solid preparation of the present invention is preferably made of two or more layers. It is preferred that a content of the polyphosphoric acid or salt thereof in a layer (1) which dissolves earlier (which may hereinafter be called Layer (1)) is greater than that of the gum tragacanth and a content of the gum tragacanth contained in a layer (2) which is brought into contact with the oral cavity later than Layer (1) or dissolves later than Layer (1) (which may hereinafter be called Layer (2)) is greater than that of the polyphosphoric acid or salt thereof. The content of the polyphosphoric acid or salt thereof in Layer (1) is preferably from 0.002 to 20 mass %, more preferably from 0.02 to 10 mass %, even more preferably from 0.2 to 4 mass %. In the case where there are two or more Layers (1), Layer (1) to be brought into contact with the oral cavity first has a content falling within the above-described range. Moreover, the content of the gum tragacanth in Layer (2) is preferably from 0.002 to 20 mass %, more preferably from 0.2 to 20 mass %, even more preferably from 0.2 to 10 mass %. The content of the polyphosphoric acid or salt thereof in Layer (2) is preferably from 0 to 10 mass %, more preferably from 0 to 2 mass %, even more preferably from 0 to 1 mass %.

It is preferred that Layer (1) contains mainly the polyphosphoric acid or salt thereof, while Layer (2) is composed of the gum tragacanth.

The sugar alcohol is preferably contained in Layer (1) because it improves the taste of the preparation and disperses the aggregate of bacteria, thereby cleaning the oral cavity. A content of the sugar alcohol in Layer (1) is preferably from 25 to 90 mass %. It is more preferably from 30 to 85 mass %, even more preferably from 32 to 70 mass %, even more preferably from 35 to 50 mass % from the viewpoint of plaque formation inhibition, the cleaning effect, and strength of the preparation.

Figure 2:
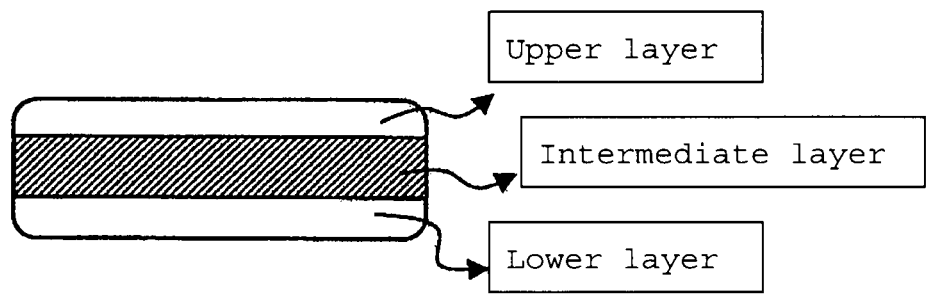
FIG. 2 is a cross-sectional schematic view of a solid preparation having a three layer structure.

Examples of the solid preparation according to the present invention include; (i) a solid preparation having an inner layer and an outer layer wherein a relative concentration of the polyphosphoric acid or salt thereof in the outer layer (Layer (1)) is made higher while a relative concentration of the gum tragacanth in the inner layer (Layer (2)) is made higher (refer to FIG. 1); and (ii) a solid preparation having a stratified structure of three or more layers wherein a relative concentration of the gum tragacanth in an intermediate layer (Layer (2)) is made higher and a relative concentration of the polyphosphoric acid or salt thereof in each of the upper and lower layers (Layer (1)) is made higher (refer to FIG. 2).

Figure 3:
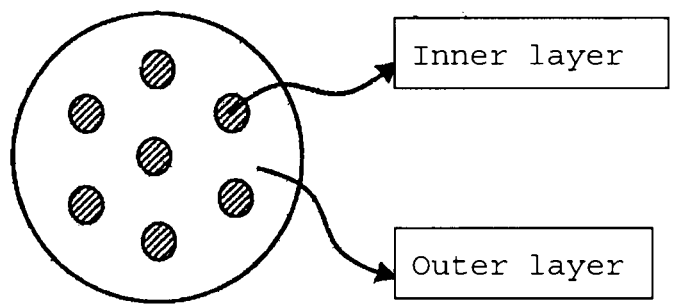
FIG. 3 is a cross-sectional schematic view of a solid preparation having an inner layer and an outer layer.

The solid preparation of the present invention can be prepared in a manner known per se in the art. Stratified tablets having, for example, three layers can be prepared by forming a layer having a high relative concentration of the polyphosphoric acid or salt thereof, forming thereover a layer having a high relative concentration of the gum tragacanth, and then forming thereover a layer having a high relative concentration of the polyphosphoric acid or salt thereof. A solid preparation having an inner layer and an outer layer can be prepared by forming an inner layer having a high relative concentration of the gum tragacanth and then covering the periphery of the inner layer with an outer layer having a high relative concentration of the polyphosphoric acid or salt thereof. It is also possible to form two or more inner layers having a high relative concentration of the gum tragacanth in an outer layer having a high relative concentration of the polyphosphoric acid or salt thereof (FIG. 3). The term "relative concentration" as used herein means a relative concentration between the gum tragacanth and the polyphosphoric acid or salt thereof.

EXAMPLES

Example 1

Composition A was prepared by mixing 40 g of erythritol, 40 g of maltitol, 17 g of corn starch, 1 g of sodium pyrophosphate, 1 g of sucrose fatty acid ester, and 1 g of a flavor. Composition B was then prepared by mixing 5 g of erythritol, 1 g of gum tragacanth, 93 g of maltitol, 1 g of a sucrose fatty acid ester, and 1 g of a flavor. After 0.2 g of Composition A was put in a tablet die, 0.4 g of Composition B and 0.2 g of Composition A were put in the tablet die successively. The resulting mixture was tableted into a solid preparation for oral application by using a hydraulic press (Riken R-301).

Comparative Example 1

A composition was prepared by mixing 80 g of sorbitol, 18 g of corn starch, 1 g of a sucrose fatty acid ester, and 1 g of a flavor. After 0.8 g of the resulting composition was put in a tablet die, it was tableted into a solid preparation for oral application by using a hydraulic press (Riken R-301).

Comparative Example 2

Composition A was prepared by mixing 80 g of maltitol, 17 g of corn starch, 1 g of sodium pyrophosphate, 1 g of a sucrose fatty acid ester, and 1 g of a flavor. Composition B was then prepared by mixing 97 g of maltitol, 1 g of gum tragacanth, 1 g of a sucrose fatty acid ester, and 1 g of a flavor. After 0.2 g of Composition A was put in a tablet die, 0.4 g of Composition B and 0.2 g of Composition A were put in the tablet die successively. The resulting mixture was tableted into a solid preparation for oral application by using a hydraulic press (Riken R-301).

Comparative Example 3

A composition was prepared by mixing 80 g of erythritol, 1 g of gum tragacanth, 1 g of sodium polyphosphate, 16 g of crystalline cellulose, 1 g of a sucrose fatty acid ester, and 1 g of a flavor. The resulting composition (1 g) was tableted into a solid preparation for oral application by using a hydraulic press (Riken R-301).

Referential Example 1

Test on Bacteria Adsorption Inhibition

An inhibiting effect of Component (b), that is, a bacteria adsorption effect by a bacteria adsorption inhibiting component was analyzed by the following method.

Stock strains of *S. mutans* (10 μCi/mL) isolated from a human oral cavity were inoculated on a brain heart infusion medium (product of DIFCO) containing 10 mL of methylated [$^3$H]-thymidine and 0.2 wt. % of glucose and cultured anaerobically at 37° C. for 24 hours. After washing with a buffer KCl solution (50 mM potassium chloride, 1 mM magnesium chloride, 1 mM phosphate buffer containing 0.1 mM magnesium chloride) three times, the resulting culture was dispersed at a concentration of $1 \times 10^9$ CFU/mL in the buffer potassium chloride solution containing 5 mg/mL bovine serum albumin to yield a $^3$H labeled *S. mutans* solution.

A 1 cm×1 cm×2 mm hydroxyapatite flat plate (product of Asahi Optical) was treated with 1 mL of each of aqueous solutions containing a bacteria adsorption inhibiting component at varied concentrations. After washing with 2 mL of the buffer potassium chloride solution, the plate was treated overnight at 4° C. in 0.5 mL of parotid saliva collected from a normal male subject. After washing twice with 2 mL of the buffer potassium chloride solution, 0.5 mL of the buffer potassium chloride solution containing 5 mg/mL bovine serum albumin and 0.5 mL of the $^3$H labeled *S. mutans* solution were added and the flat plate was treated at 37° C. for 1 hour. After washing three times with the buffer potassium chloride solution, the hydroxy apatite flat plate was treated at 70° C. for one hour in 1 mL of 2 M/L sodium hydroxide. After neutralization with 1 mL of 2N hydrochloric acid, $^3$H radioactivity was measured using a liquid scintillation counter and the number (X) of bacteria adsorbed to the flat plate was determined.

The number of bacteria adsorbed to the flat plate when a similar treatment to the treatment in the above operation was performed using 1 mL of distilled water instead of the aqueous solution is designated as A.

The number of bacteria adsorbed to the flat plate when a similar treatment to the treatment in the above operation was performed using 1 mL of distilled water instead of the aqueous solution and 0.5 mL of the buffered potassium chloride solution instead of the parotid saliva is designated as B.

$$\text{Bacteria adsorption inhibition percentage } I(\%) = (A-X)/(A-B) \times 100 \quad \text{(Equation 1)}$$

The bacteria adsorption inhibition percentage of a 0.1 mass % aqueous solution of gum tragacanth was 86.1%.

Test 1

The tooth surfaces of eight normal male subjects were cleaned by a dental hygienist. On the day, the male subjects were asked to lick one tablet (Example 1 and Comparative Examples 1 and 3) without chewing, and to continue licking for one minute (30 seconds for each of the right side and the left side of the tablet) without swallowing the saliva and after completion of licking, swallowed the saliva. This cycle was repeated. The above operation was repeated 6 times a day (after every meal, 10:00, 15:00, and before bedtime). On the second day, similar administration was performed. After administration for two days, an amount of the plaque formed for 48 hours after cleaning of the tooth surface was measured. The amount of plaque was scored by dividing one tooth into 5 parts. The plaque formation inhibition of the subjects was evaluated under a double blind cross-over method. The plaque formation inhibition percentage (%) is determined by the following equation. The results are shown in FIG. 4.

Plaque formation inhibition percentage(%)=(formation amount of plaque in Comparative Example 1−formation amount of plaque of an evaluated sample)/formation amount of plaque in Comparative Example 1×100  (Equation 2)

Figure 4:
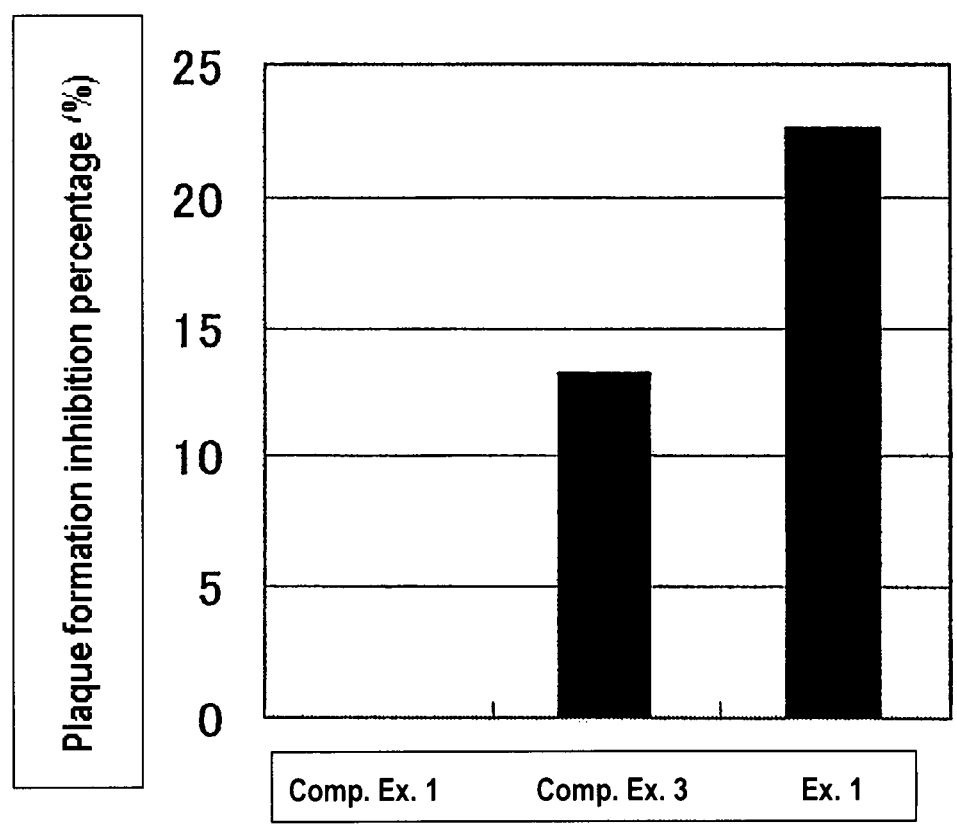
FIG. 4 shows a plaque formation inhibiting effect brought about by the combined use of gum tragacanth and a pyrophosphoric acid (Example 1).

It has been found from FIG. 4 that the solid preparation of the present invention obtained in Example 1 had an excellent plaque formation inhibiting effect approximately 1.4 times as much as that of Comparative Example 3 in which Components (a) and (b) were applied simultaneously. The preparation obtained in Comparative Example 3 showed a better plaque formation inhibiting effect than the preparation obtained in Comparative Example 1 containing neither Component (a) nor Component (b).

Test 2: Evaluation of Taste

Taste of each of the solid preparations prepared in Example 1 and Comparative Examples 1, 2, and 3 was evaluated in accordance with the following criteria by three normal male subjects. The results are shown in Table 1.

A: The preparation is good to the taste.
B: The preparation leaves a harsh taste.

As a result, as shown in Table 1, the solid preparation using, in combination, the polyphosphoric acid or salt thereof and a sugar alcohol having no cool feeling leaves a harsh taste due to the warmth of the polyphosphoric acid or salt thereof. It is therefore rated as B. It has been found, on the other hand, that when polyphosphoric acid or salt thereof and a sugar alcohol having a cool feeling dissolve simultaneously, the resulting preparation is good to the taste.

TABLE 1

|  | Comparative Example 1 | Comparative Example 2 | Comparative Example 3 | Example 1 |
|---|---|---|---|---|
| Subject 1 | A | B | A | A |
| Subject 2 | A | B | A | A |
| Subject 3 | A | B | A | A |
| Results | A | B | A | A |

The invention claimed is:

1. A solid preparation for oral application comprising (a) gum tragacanth and (b) at least one polyphosphoric acid or a salt thereof, wherein
   the solid preparation is made of two or more layers,
   a content of (b) the at least one polyphosphoric acid or a salt thereof in a first layer (1) is from 0.002 to 20 mass % and is greater than that of (a) the gum tragacanth and (b) the at least one polyphosphoric acid or a salt thereof dissolves earlier than said (a) gum tragacanth and,
   a content of (a) the gum tragacanth contained in a second layer (2) which is brought into contact with the oral cavity later than said layer (1) or dissolves later than said layer (1) is from 0.002 to 20 mass % and is greater than that of (b) the at least one polyphosphoric acid or a salt thereof,
   wherein the solid preparation is in a tablet, pill, or granular form.

2. The solid preparation for oral application according to claim 1, further comprising (c) at least one sugar alcohol selected from the group consisting of erythritol, xylitol, and sorbitol.

3. The solid preparation for oral application according to claim 2, which is constituted so that the at least one polyphosphoric acid or a salt thereof and the at least one sugar alcohol (c) start to dissolve simultaneously.

4. The solid preparation for oral application according to claim 1, wherein the at least one polyphosphoric acid or a salt thereof is selected from the group consisting of pyrophosphoric acid, acidic pyrophosphoric acid, tripolyphosphoric acid, a salt thereof, and a mixture thereof.

5. The solid preparation for oral application according to claim 3, wherein the at least one polyphosphoric acid or a salt thereof is selected from the group consisting of pyrophosphoric acid, acidic pyrophosphoric acid, tripolyphosphoric acid, a salt thereof, and a mixture thereof.

6. The solid preparation for oral application according to claim 1, wherein the layer (1) is an outer layer and the layer (2) is an inner layer.

7. The solid preparation for oral application according to claim 1, wherein solid preparation is in the tablet form which includes an outer layer and the plurality of inner layers, and wherein each of the inner layers is entirely enclosed within the outer layer and does not contact the outer surface of the outer layer, and wherein the outer layer is the first layer and the plurality of the inner layers is the second layer.

8. The solid preparation for oral application according to claim 1, wherein the solid preparation is in the tablet form which includes an inner layer and an outer layer, wherein the outside surface of the inner layer does not contact the outside surface of the outer layer, and wherein the outer layer is the first layer and the inner layer is the second layer.

9. The solid preparation for oral application according to claim 1, wherein the solid preparation is in the tablet form which includes an upper layer, a lower layer, and an intermediate layer between the upper and lower layers, wherein the intermediate layer is the second layer, and the upper and lower layers are the first layer.

10. The solid preparation for oral application according to claim 1, wherein the solid preparation is in the tablet form which includes an outer layer and the plurality of inner layers, and wherein the outer layer is the first layer and the plurality of the inner layers is the second layer.

11. The solid preparation for oral application according to claim 1, wherein the content of the at least one polyphosphoric acid or a salt thereof in the second layer is from 0.002 to 10 mass %.

12. The solid preparation for oral application according to claim 1, wherein the solid preparation is in the tablet form.

13. A method of inhibiting plaque formation comprising applying a solid preparation comprising (a) gum tragacanth and (b) at least one polyphosphoric acid or a salt thereof to an oral cavity, wherein the at least one polyphosphoric acid or a salt thereof (b) is applied prior to the application of the gum tragacanth (a),
   wherein the solid preparation is made of two or more layers,
   a content of (b) the at least one polyphosphoric acid or a salt thereof in a first layer (1) is from 0.002 to 20 mass % and is greater than that of (a) the gum tragacanth and said (b) the at least one polyphosphoric acid or a salt thereof dissolves earlier than said (a) gum tragacanth and,
   a content of (a) the gum tragacanth contained in a second layer (2) which is brought into contact with the oral cavity later than said layer (1) or dissolves later than said layer (1) is from 0.002 to 20 mass % and is greater than that of (b) the at least one polyphosphoric acid or a salt thereof, wherein the solid preparation is in a tablet, pill, or granular form.

14. The method according to claim 13, wherein said solid preparation further comprises (c) at least one sugar alcohol selected from the group consisting of erythritol, xylitol, and sorbitol.

15. The method according to claim 13, wherein the at least one polyphosphoric acid or a salt thereof is selected from the group consisting of pyrophosphoric acid, acidic pyrophosphoric acid, tripolyphosphoric acid, a salt thereof, and a mixture thereof.

16. The method according to claim 13, wherein the solid preparation is in the tablet form.

\* \* \* \* \*